(12) United States Patent
Montague

(10) Patent No.: US 11,712,306 B2
(45) Date of Patent: Aug. 1, 2023

(54) OPTICAL COHERENCE TOMOGRAPHY FOR ROBOTIC BRAIN SURGERY

(71) Applicant: Neuralink Corp., Fremont, CA (US)

(72) Inventor: Gilbert I. Montague, Pacifica, CA (US)

(73) Assignee: Neuralink Corp., Fremont, CA (US)

(*) Notice: Subject to any disclaimer, the term of this patent is extended or adjusted under 35 U.S.C. 154(b) by 421 days.

(21) Appl. No.: 16/922,823

(22) Filed: Jul. 7, 2020

(65) Prior Publication Data

US 2021/0007808 A1 Jan. 14, 2021

Related U.S. Application Data

(60) Provisional application No. 62/873,705, filed on Jul. 12, 2019.

(51) Int. Cl.
*A61B 34/30* (2016.01)
*A61B 5/00* (2006.01)
(Continued)

(52) U.S. Cl.
CPC ............. *A61B 34/20* (2016.02); *A61B 34/30* (2016.02); *G06T 7/12* (2017.01);
(Continued)

(58) Field of Classification Search
None
See application file for complete search history.

(56) References Cited

U.S. PATENT DOCUMENTS

| 5,215,095 A | * | 6/1993 | Macvicar | ............... | A61B 90/36 600/425 |
| 6,901,171 B1 | * | 5/2005 | Dutta-Choudhury | ..... | G06T 7/12 382/199 |

(Continued)

FOREIGN PATENT DOCUMENTS

| JP | 2017099757 A | 6/2017 |
| JP | 2018089055 A | 6/2018 |

(Continued)

OTHER PUBLICATIONS

Matteo De Silvestri, "Real-time Haptic Guidance System for Retinal Surgery Based on Intraoperative Optical Coherence Tomography," University of Illinois at Chicago MS Thesis, 2018 (Year: 2018).*

(Continued)

*Primary Examiner* — Soo Shin
(74) *Attorney, Agent, or Firm* — Kilpatrick Townsend & Stockton LLP

(57) ABSTRACT

Disclosed are methods related to guiding robotic surgery using optical coherence tomography (OCT) and computer-readable media and computer systems executing the methods. They may include receiving a series of cross-sectional slices of 3D space obtained from an OCT probe over biological tissue and processing and filtering the series of slices. The processing and filtering may include spatially smoothing the intensity values of each slice, thresholding each slice after it has been blurred, performing a connected-component analysis to identify blobs on the thresholded slice, filtering the blobs, performing edge detection, and invoking a selective median filter. The processing and filtering can be used to construct a depth map from the received series of cross-sectional slices in order to guide a robotic end effector, based on the depth map.

20 Claims, 15 Drawing Sheets

(51) Int. Cl.
  *A61B 90/00* (2016.01)
  *A61B 90/11* (2016.01)
  *A61B 90/30* (2016.01)
  *A61N 1/05* (2006.01)
  *A61N 1/36* (2006.01)
  *G06T 5/00* (2006.01)
  *G06T 7/11* (2017.01)
  *G06T 7/12* (2017.01)
  *G06T 7/187* (2017.01)
  *G06T 7/564* (2017.01)
  *A61B 34/20* (2016.01)

(52) U.S. Cl.
  CPC . *A61B 2090/309* (2016.02); *A61B 2090/3735* (2016.02); *G06T 2207/10101* (2013.01); *G06T 2207/30016* (2013.01)

(56) References Cited

U.S. PATENT DOCUMENTS

| | | | |
|---|---|---|---|
| 8,707,734 B2 | 4/2014 | Haque et al. | |
| 9,430,827 B2* | 8/2016 | Kelm | G06T 7/143 |
| 10,838,210 B2* | 11/2020 | Robaina | A61B 90/36 |
| 11,439,811 B2* | 9/2022 | de Miguel, Sr. | A61N 1/08 |
| 11,478,308 B2* | 10/2022 | Hoffman | A61B 34/37 |
| 2008/0292194 A1 | 11/2008 | Schmidt et al. | |
| 2011/0144480 A1 | 6/2011 | Lu | |
| 2012/0035434 A1* | 2/2012 | Ferren | A61B 5/4839 600/301 |
| 2013/0194546 A1* | 8/2013 | Iwase | G06T 7/0012 351/246 |
| 2014/0187922 A1 | 7/2014 | Mark et al. | |
| 2014/0267603 A1 | 9/2014 | Kerdok et al. | |
| 2014/0320392 A1 | 10/2014 | Chizeck et al. | |
| 2015/0187085 A1* | 7/2015 | Ihara | G06T 7/12 382/128 |
| 2015/0223765 A1 | 8/2015 | Chopra | |
| 2020/0085375 A1 | 3/2020 | Tolosa et al. | |
| 2020/0086111 A1 | 3/2020 | Young et al. | |
| 2021/0251490 A1* | 8/2021 | Abdolmanafi | G06V 10/454 |
| 2022/0273450 A1* | 9/2022 | Steines | A61F 2/30 |
| 2022/0322973 A1* | 10/2022 | Seemann | A61B 34/20 |

FOREIGN PATENT DOCUMENTS

| | | |
|---|---|---|
| JP | 2018189371 A | 11/2018 |
| JP | 6791007 A | 11/2020 |

OTHER PUBLICATIONS

Haoran Yu, "OCT Guided Micro-Vascular Robotic Surgery: Design, Calibration and Telemanipulation," Vanderbilt University PhD Dissertation, 2016 (Year: 2016).*

Chung et al., A Polymer Probe-Based System for High Density, Long-Lasting Electrophysiological Recordings Across Distributed Neuronal Circuits, http://dx.doi.org/10.1101/242693, Jan. 4, 2018.

P. Merz et al., A Novel Micromachining Technology for Structuring Borosilicate Glass Substrates, Transducers '03, pp. 258-261, Fraunhofer Institute for Silicon Technology (FHG ISIT), Itzehoe, Germany.

A. Tooker et al., "Towards a Large-Scale Recording System: Demonstration of Polymer-Based Penetrating Array for Chronic Neural Recording," 36th Annual International Conference of the IEEE Engineering in Medicine and Biology Society, Aug. 2014, LLNL-CONF-655518, Chicago, IL.

Application No. PCT/US2020/041056, International Search Report and Written Opinion, dated On Oct. 13, 2020, 7 pages.

Desilvestri, Matteo, Real-Time Haptic Guidance System for Retinal Surgery Based on Intraoperative Optical Coherence Tomography, the U.S. University of Illinois at Chicago. Thesis. Aug. 16, 2018, https://indigo.uic.edu/articles/thesis/Real-Time_Haptic_Guidance_System_for_Retinal_Surgery_Based_on_Intraoperative_Coherence_Tomography/10877258.

Application No. JP2021-576739, Notice of Allowance, dated Dec. 13, 2022, 1 page.

* cited by examiner

OPTICAL COHERENCE TOMOGRAPHY FOR ROBOTIC BRAIN SURGERY

CROSS-REFERENCES TO RELATED APPLICATIONS

This application claims priority from U.S. Patent Application No. 62/873,705, filed Jul. 12, 2019, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

The present application generally relates to optical coherence tomography (OCT), including its use as a sensor for guiding robotic surgical systems. Specifically, the application is related to techniques for adapting OCT for real-time use in acquiring depth maps of a wet brain surface or other tissue surface for robotic insertion of electrodes.

2. Description of the Related Art

Devices exist that can be implanted into biological membranes such as the brain. In certain instances, the implantable device has a biocompatible substrate with conduits, such as electrodes, for stimulation of neurons and/or recording neuronal signals.

Brain implants require delicate control to securely insert and attach an implant and all of the respective connection points to the brain. Several challenges exist in surgically implanting a brain implant, including but not limited to avoiding vasculature, while also making successful physical and electrical connections into the brain.

International Patent Application Publication No. WO 2016/126340, published Aug. 11, 2016, discloses implantable devices that can be implanted into the brain of a subject and used for a variety of purposes. The implantable device can have conduits or electrodes that can record or deliver stimulation, such as light, current, voltage, or drugs.

In certain implementations, and particularly with progression of modern medicine, surgical robots are becoming an assistive tool for implantation procedures. Given the limited access to the brain as well as the complex structure of the brain, computer vision for surgical robots becomes a problem in differentiating the varying layers of the brain as well as discerning shadows that may be cast by surgery tools, portions of the implant, or perhaps even the surgical robot itself.

For brain implants utilizing electrodes, implantation with specific accuracy becomes difficult spatially in terms of accommodating for underlying background movement, such as blood flow, heart rate, breathing, and natural brain movement. This may be compounded by the presence of a fluid membrane on the surface of the brain as well as distinguishing between the proper depth to implant as more neurons are added.

Leveraging the accuracy of a surgical robot is desirable in operations involving delicate organs, such as the brain.

There is a need in the art for a more precise, real-time brain electrode implantation method to connect to implantable devices.

BRIEF SUMMARY

Generally, a robotic surgery system uses optical coherence tomography (OCT) to facilitate implanting biocompatible electrodes in biological tissue (e.g., neurological tissue such as the brain) using robotic assemblies. Real-time OCT helps guide the robotic surgery system, which includes components to engage an implantable device, identify a target implantation site, and verify insertion. The system attaches, via robotic manipulation, the electrode to an engagement element of an insertion needle. The OCT illuminates the first few hundred microns of brain tissue with suitable wavelengths of light, obtain 2-dimensional slices of the brain vasculature and other features, processes the slices to find a depth map based on the known layering of brain tissue, and presents the depth map so that the surgical robot may implant the electrode via robotic assembly.

In utilizing OCT to facilitate implanting biocompatible electrodes, to best ensure precision and accuracy throughout the operation, the OCT must be adaptive to the brain's dynamic environment. As a result, filtering out and ensuring correct guidance to the implantation site are important to providing a successful operation.

The method of guiding robotic surgery may start with receiving a series of cross-sectional 3-dimensional (3D) space obtained from an optical coherence tomography (OCT) probe over biological tissue, with each slice including a 2-dimensional array of intensity values. Next, the intensity values in each slice may be spatially smoothed to produce a corresponding blurred slice. Next, the blurred slice may be thresholded to create a corresponding segmented slice. Next, a connected-component analysis may be performed on each segmented slice to identify blobs on the respective segmented slice. Next, the blobs may be filtered at least on a size of the blobs. Next, the filtered blobs may have edge detection run to construct a corresponding edge detection slice. Next, a selective median filter may be invoked on the edge detection slices to construct a depth map of a surface of the biological tissue. Next, a robotic end effector can be guided based on the depth map.

In some embodiments, the method may also include removing from consideration a segmented slice whose largest blob does not project at least 50% across the respective segmented slice. In some embodiments, the method may remove the segmented slice whose blob does not project at least 75% across the respective segmented slice.

In some embodiments, filtering out blobs may reject a blob corresponding to an electrical wire protruding from the biological tissue.

In some embodiments, the biological tissue may be the brain cortex covered with pia-arachnoid complex.

In some embodiments, the spatially smoothing may include Gaussian blurring or median blurring.

In some embodiments, the thresholding may involve dynamically selecting threshold values using Otsu's method to minimize intra-class intensity variance.

In some embodiments, the method may include selecting the series of slices from a larger set of OCT slices.

In some embodiments, the edge detecting may result in more than one continuous edge in each edge detection slice.

In some embodiments, the selective median filter may create multiple depth maps of surfaces of the tissue. In some embodiments, the method may include selecting a top surface depth map.

In some embodiments, a non-transitory computer-readable medium may store computer-executable instructions that, when executed by a processor, cause the processor to perform, and/or to instruct the components of the system to perform, any of the methods described above for guiding robotic surgery.

DETAILED DESCRIPTION

Optical coherence tomography (OCT) can be used in real-time control of a robotic arm for surgery. Specifically, OCT works well for determining where vasculature is in the outermost layers of the brain—which are transparent or translucent to the light used for OCT to a depth of about 100 μm (microns). Additionally, OCT works through blood or other fluids that obfuscate the field.

Commercially available OCT visualization systems, which is used by optometrists, are generally too slow for real-time control. For example, it takes a few seconds to scan and display portions of a patient's eye. Updates on the order of a few seconds are too slow for real-time robotic operations, even with a sedated subject.

Because of the way certain layers and features of the meninges appear in OCT data, one can use these features to accelerate the determination of those features and guide a robotically guided needle or other end effector.

System Overview

Figure 1A:
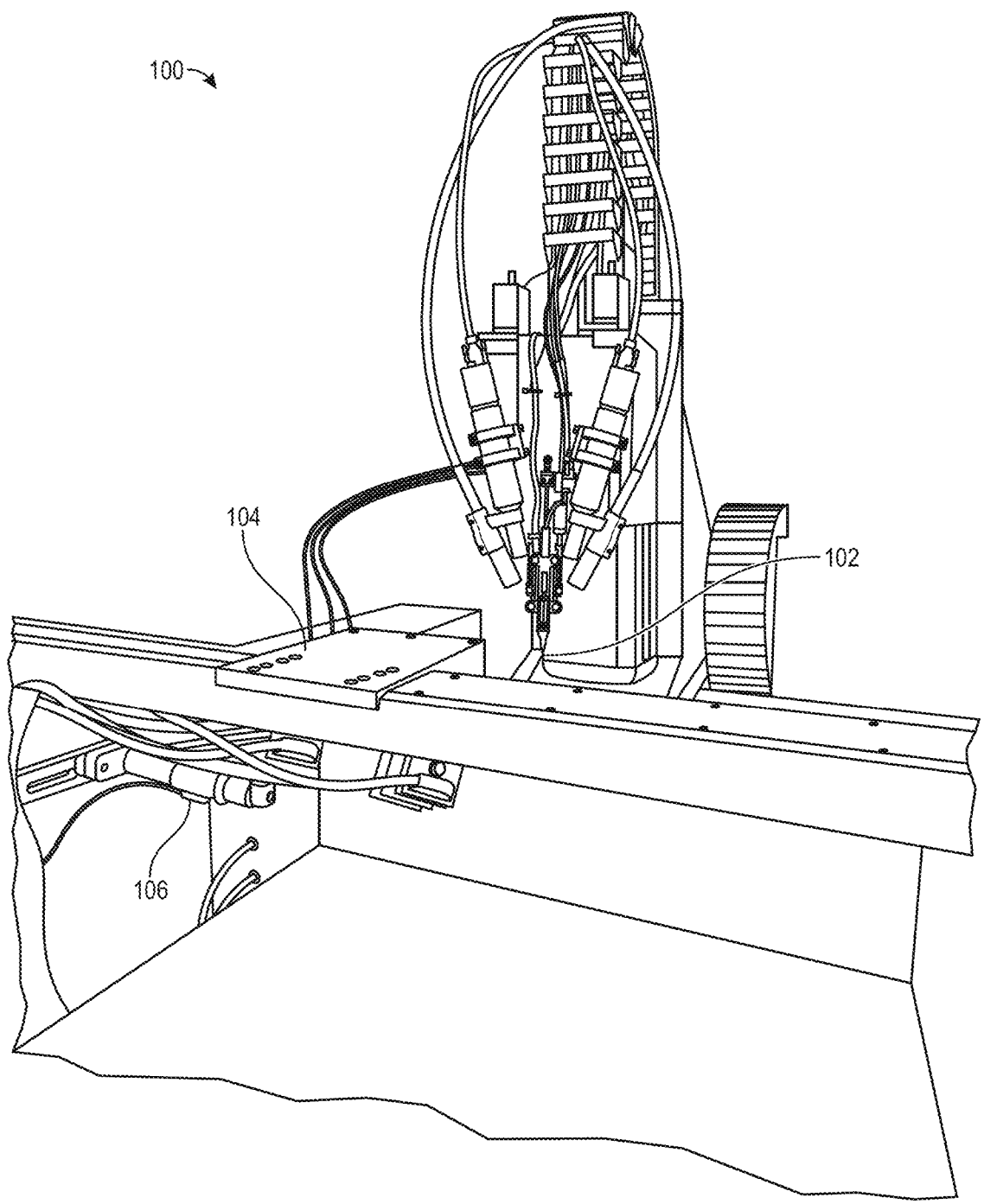
FIG. 1A is a robotic surgery system using optical coherence tomography (OCT), according to embodiments.
Figure 1B:
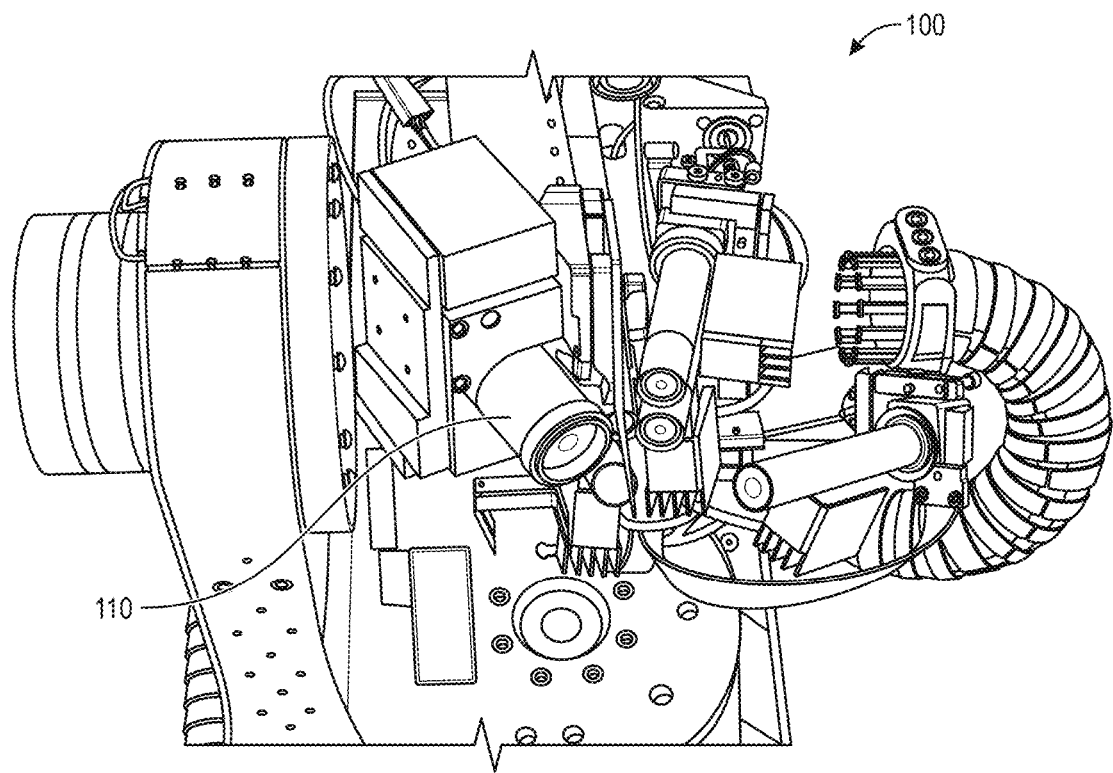
FIG. 1B illustrates a close up bottom view of the system of FIG. 1A.

FIG. 1A illustrates an example system 100 for robotic surgical implantation of an electrode device, according to embodiments. FIG. 1B illustrates a close up bottom view of example system 100 for robotic surgical implantation of an electrode, according to embodiments. In some embodiments, the entire system 100 may be associated with a robot, for example a single robot may be integrated together with all the components of system 100. In some embodiments, some sub-systems of system 100 may be combined, for example a single robot may include an inserter head 102 that can also perform the functions of device engagement sub-system 104, and is not limited by the present disclosure.

In this example, system 100 includes an inserter head 102 and device engagement sub-system 104. Device engagement sub-system 104 can engage electrodes for implantation, and inserter head 102 can perform targeting and/or insertion verification functions while implanting the electrodes in neurological tissue, as described herein below. Inserter head 102 may also be referred to as a targeting and/or insertion verification sub-system, and device engagement sub-system 104 may also be referred to as an electrode stage. In some embodiments, the functions of inserter head 102 and device engagement sub-system 104 can instead be performed by a single apparatus. For example, in some embodiments, the functions of device engagement sub-system 104 may be performed by components of inserter head 102. System 100 may further include ultrasonic cleaner 106.

System 100 and/or sub-system 104 can contain light sources configured to illuminate the electrode device and system 100 and/or sub-system 102 can contain light sources configured to illuminate the surgical field. The light sources illuminating the electrode device or an insertion needle can produce light of wavelengths selected based on a material associated with the electrode device or needle, while the light sources illuminating the surgical field can produce light of wavelengths chosen for imaging the target tissue. In particular, system 100 may contain multiple independent light modules, each capable of independently illuminating with 405 nm, 525 nm and 650 nm or white light. For example, if the implantable electrode device contains a bio-compatible substrate made from polyimide, the wavelength of the light from the light source may be between 390 nm and 425 nm (e.g., 405 nm or 395 nm). In an embodiment, the light sources may include a laser and/or a light emitting diode (LED). In an embodiment, the implantable electrode device can contain a bio-compatible substrate made from polyimide, polyamide, and/or another aromatic rigid chain polymer material, fluorescent material, or other material, and is not limited by the present disclosure.

System 100 can contain cameras configured to obtain images, such as digital photos, of the electrode device and an insertion needle, and cameras configured to obtain images of the target neurological tissue, e.g. a brain cortex. In another example, the images can include images of any subject relevant to robotic surgical implantation. In a typical embodiment, the cameras can include two cameras arranged at a relative angle (e.g., a relative angle substantially equal to 45°, or some other angle). In various embodiments, system 100 can contain additional cameras, or other sensors, such as video cameras, microphones, chemical sensors, temperature sensors, time sensors, and force or pressure sensors, and is not limited by the present disclosure.

The light sources may include one or more light sources that can be cycled or strobed between illuminated and extinguished states, and/or among different wavelengths of light, so that the cameras can image different perspectives or aspects of the surgical field. In an embodiment, the cameras can be cooled in order to increase their sensitivity, such as to faint fluorescent light. In one embodiment, one or more of the cameras may be integrated into a microscope. In embodiments, the light sources may be suitable for interferometry, such as that used in optical coherence tomography.

In embodiments where the light sources are suitable for interferometry, such as that used in optical coherence tomography, a sensor may be used for the interferometry. The sensor may acquire and transmit data on the order of, for example, 30 gBits/sec.

System 100 can include a processing unit, such as computing system 1800 in the example of FIG. 18A below, configured to execute a computer vision heuristic to process the images obtained by the cameras. The computing system may be communicatively coupled to a plurality of cameras configured to image one or more portions of the surgical field and/or the electrode device and needle. In particular, the computing system can apply computer vision techniques to images from the cameras in order to determine the location and/or orientation of the electrode device. In an embodiment, the computing system can determine locations and/or orientations of an insertion needle and a target tissue for implantation. In embodiments, the processing unit may be suitable for processing and extracting surface data acquired from, for example, the optical coherence tomography data. The computing system may then process that data. For example, the computing system can determine a contour of the target surgical tissue, based on images from the cameras. In various embodiments, a processing unit can include one or more processors, one or more processing cores, one or more computing systems such as computing system 1800 in the example of FIG. 18A below, one or more GPUs, or combinations thereof, and is not limited by the present disclosure.

System 100 can contain one or more robotic assemblies, such as a robotic assembly configured to implant the electrode device surgically into target biological tissue. The robotic assemblies may be guided by a processing unit, such as computing system 1800 in the example of FIG. 18A below, based on the triangulated locations of the electrode device, an insertion needle, and/or a target tissue, determined by the computing system. In an embodiment, system 100 can further contain an additional robotic assembly configured to attach an engagement element of the insertion needle to a reciprocal engagement element on the electrode device. In an embodiment, when surgically implanting the electrode device, the robotic assemblies can surgically implant the insertion needle attached to the electrode device. The robotic assemblies can further be guided based on images from the cameras. In an embodiment, system 100 can contain other actuators, such as sonic, ultrasonic, or pressure actuators, or can guide other implements such as a scalpel, and is not limited by the present disclosure.

In some embodiments, system 100 can include additional cameras, and is not limited by the present disclosure. For example, system 100 can use a separate camera system, located on a head of a robotic assembly, for mapping the target tissue site. In some embodiments, this robotic assembly may also be configured to carry an insertion needle. The separate camera system can be movably situated on one or more axes. In an embodiment, the system drives this robotic assembly down an axis, such that a focus of the camera system is below the target tissue site of interest, such as brain tissue. The robotic assembly can move upward along the axis, and/or scan the camera system upwards, in order to image the target tissue.

In a typical embodiment of the present disclosure, robotic surgery system 100 may implant implantable devices including electrodes with improved depth penetration that are able to penetrate below the surface of biological tissue (e.g., cortex). Example electrodes may include those discussed in a U.S. Patent Publication No US 2020/0085375 A1 titled "Electrode Design and Fabrication," which is hereby incorporated by reference. The disclosed robotic system may implant implantable devices that are arranged in a pillbox, a cartridge, and/or a pillbox-cartridge assembly such as those discussed in a U.S. Patent Publication No. US 2020/0086111 A1 titled "Device Implantation Using a Cartridge," which is hereby incorporated by reference. Additionally, the disclosed robotic system may control the operation of a needle.

FIG. 1B shows a bottom view of an example system 100. The view shows an OCT sensor 110. The OCT sensor 110 may be positioned such to receive light signals from the back of a tissue sample. In embodiments, the OCT sensor 110 may be positioned to follow the inserter head 102, such that as the inserter head 102 operates on a particular region of the brain, the OCT sensor 110 is receiving visual data regarding the operating region.

Figure 2A:
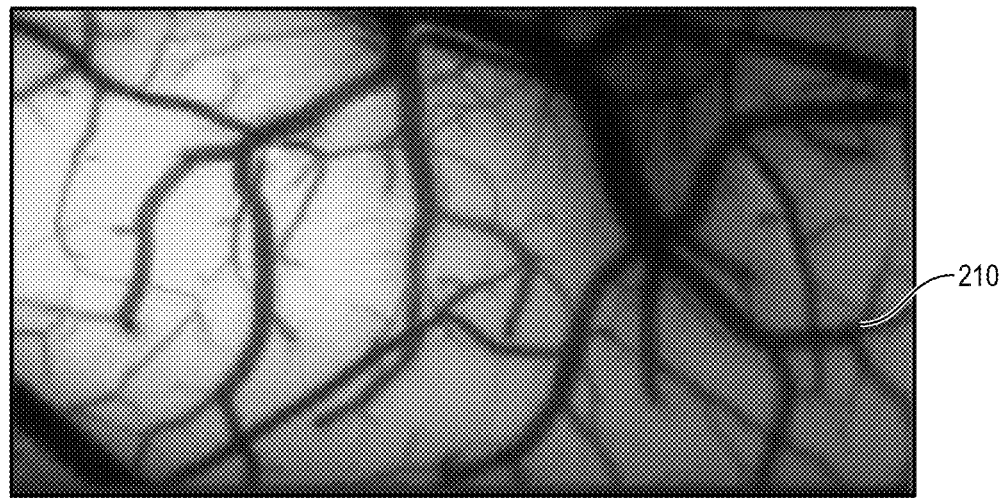
FIG. 2A is an overhead image of a portion of a brain, according to embodiments.

FIG. 2A is an image of a portion of a brain, including target insertion areas in accordance with an embodiment. One of the goals of some brain surgeries is to avoid vasculature, such as vasculature 210, the dark spidery regions within the photographs. A doctor may use these images to manually select where to insert needles in order to avoid vasculature. Automating this selection process and targeting can enable upscaling to hundreds or thousands of locations.

Figure 2B:
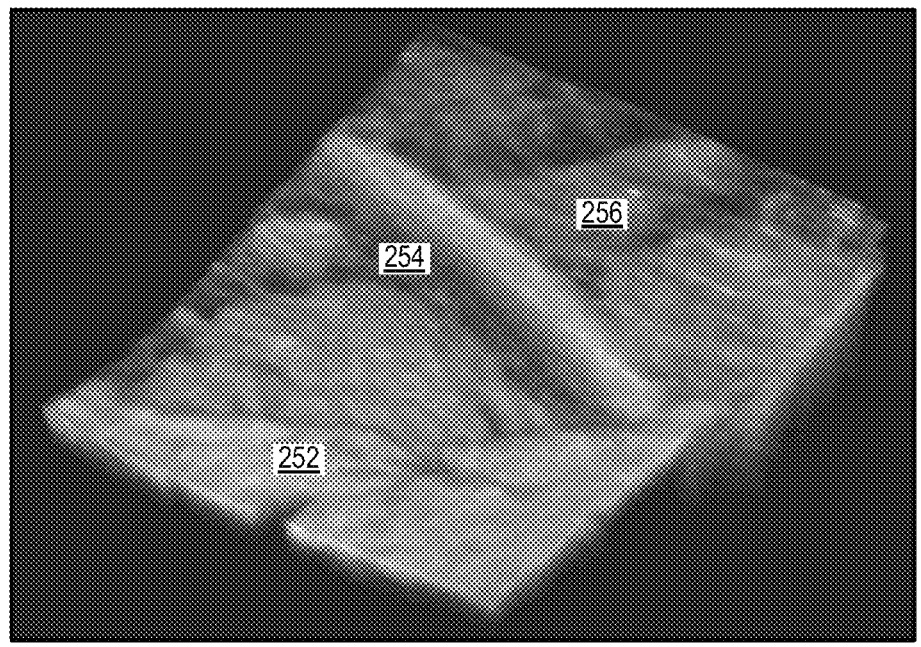
FIG. 2B is a 3D image showing surface topology of the brain of FIG. 2A.

FIG. 2B is a volume snapshot of the brain showing vessels and vasculature. The surface of the brain is a dynamic environment with pulsating vessels, flowing fluid, and pulsing layers. Due to the complexity of the environment, surgery and implantation via a robotic system must adapt for the factors that may impact precision and accuracy. The image shown in the figure depicts the surface of the brain. Region 252 is a blood vessel, region 254 is the subarachnoid space, the region 256 shows the brain surface undulating. Even with a mapping of the brain, given its dynamic, changing surface, processing and understanding the surface at speeds quick enough to instruct an inserter head, such as inserter head 102 (see FIG. 1A), may prove challenging.

Figure 3:
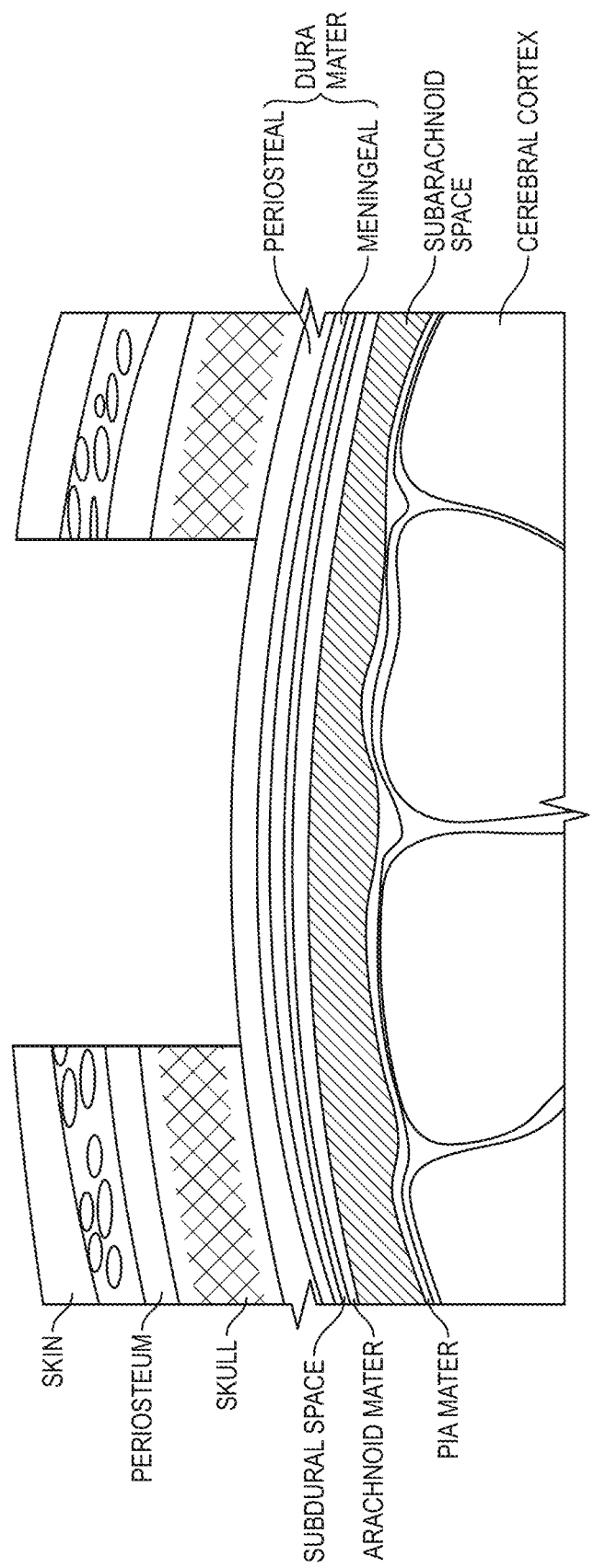
FIG. 3 is a cross section of a head with a portion of its skull removed in accordance with an embodiment.

FIG. 3 is a cross-sectional view of a mammalian brain. In one embodiment, the methods includes forming an opening in the scalp and cutting a hole through the skull and through the dura mater prior to implantation. The dura mater is made up of two layers known as the periosteum and the meningeal, which are generally referred to as only one layer or the dura layer. Next is the arachnoid layer. The arachnoid layer is a thin membrane that surrounds the brain and is separable from the dura. There is a space between the dura and the arachnoid membrane that is called the subdural space.

Below the arachnoid layer is the subarachnoid space, which is limited externally by a water-tight layer of connective tissue, the arachnoid, and internally by a thinner layer, the pia mater. It is within the subarachnoid space that CSF flows.

The pia mater adheres intimately to the surface of the brain and spinal cord. The pia mater is the layer of meninges closest to the surface of the brain. The pia mater has many blood vessels that reach deep into the surface of the brain. The major arteries supplying the brain provide the pia with its blood vessels. The space that separates the arachnoid and the pia mater is called the subarachnoid space.

Real-Time Imaging Process

Optical coherence tomography (OCT) can be used to guide a system, such as system 100 (see FIG. 1A), in surgically implanting electrodes. Due to the brain's liquid-surface layer, flowing blood, CSF, and varying layers that may cause obscuring of the light path, accurate depth of field maps that can quickly be generated to guide an inserter head are largely beneficial in ensuring precision of a surgical robot system.

In ensuring a proper depth map is generated, an OCT sensor, such as the OCT sensor 110, may begin by obtaining a stack of 2-dimensional arrays, showing intensity values that correlate to light that bounces back to the sensor of the system. In embodiments, the OCT sensor may obtain a volume of points of light intensity based off a captured reflection from a surface, such as a brain. The OCT sensor may obtain a range of points, such as 20 million, 30 million, 40 million or more points. The various points are collected into a 2-dimensional array of slices, with each slice being a different depth layer of the brain. The 2-dimensional array may consist of anywhere from 120-160 slices. From this full stack of slices, a processor, such as the processor 1800 of FIG. 18A, may narrow down and select from 10 to 30 slices based off of spatial selection received for targeted insertion cites.

Figure 4:
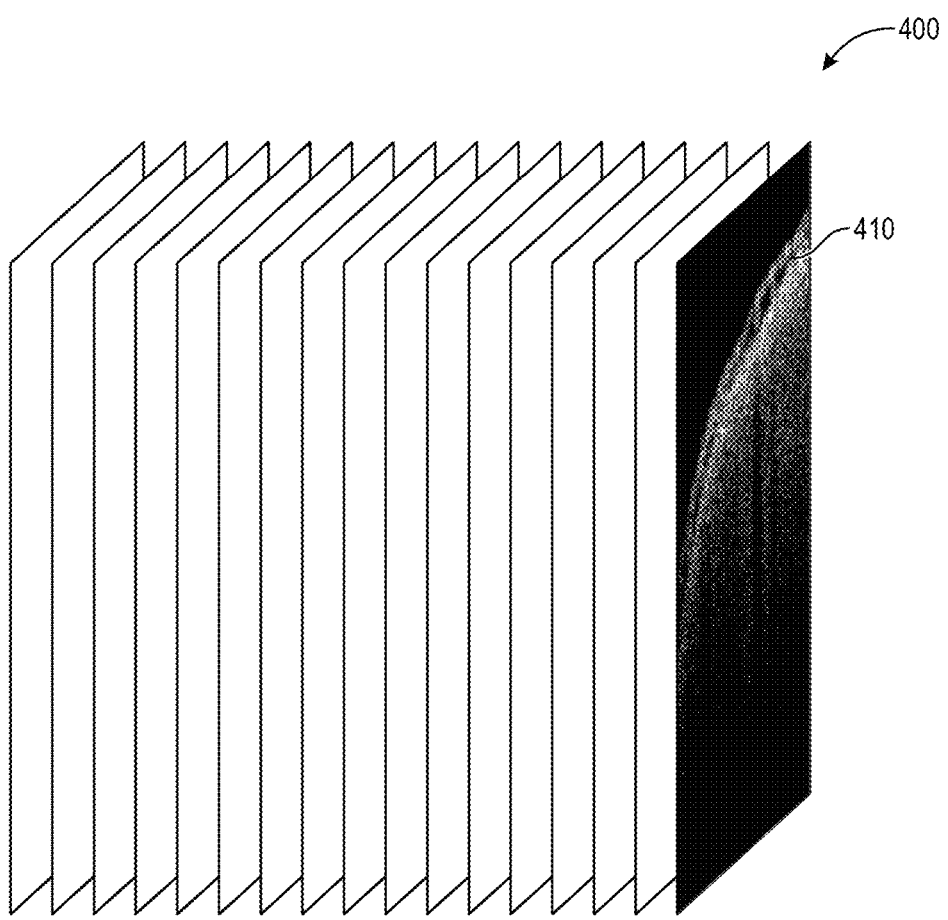
FIG. 4 is a stack of slices of 2-dimensional arrays of intensity values from a brain captured by optical coherence tomography (OCT), according to embodiments.

FIG. 4 shows a stack 400 of slices of 2-dimensional arrays of intensity values from a brain, captured by OCT, such as by the OCT sensor 110 shown in FIG. 1B. The stack 400 consists of slices 410, with each slice 410 showing the points collected by the OCT sensor. The OCT sensor would be at the top of the figure facing downward. The various points are collected into a 2-dimensional array of slices, forming a stack, such as stack 400, with each slice being a different depth layer of the brain. For example, the slice 410 on the rightmost side of the stack can show a slice imaged by OCT at a particular depth.

Figure 5:
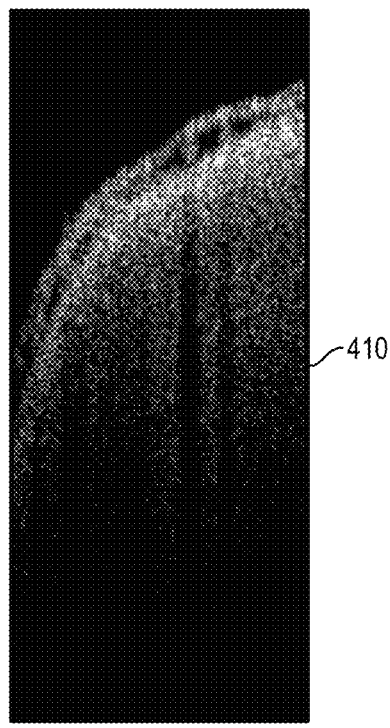
FIG. 5 is one of the slices of FIG. 4.

FIG. 5 shows an exemplary slice 410 of the stack 400. The slice 410 may have an array of intensity values as measured by OCT. Each slice 410 shows a cross-section of the brain along the X-Y plane, with the OCT sensor looking down from the top. Thus, a stack of slices would form a depth of the brain with corresponding intensity values along the depth.

However, OCT may pick up background signal, noise and other artifacts in the captured slice 410. In order to filter out low signal and noise, a smoothing method may be applied.

A processing unit, such as processing unit 1800 (see FIG. 18A), may use processing and filtering methods on each slice to generate a depth map that guides a surgical robot in implanting operations.

As the intensity points represent discrete locations on each slice, a processing unit may encounter problems identifying regions that form part of the surface as opposed to voids, such as noise, low signal, or artifacts. In order to correct for this, a processing unit may implement a smoothing filter to obtain a smoother image relative to the array of intensity points. In embodiments, the smoothing can be a Gaussian blur, a median blur, a bilateral filter, or other spatially smoothing algorithms. The processing unit may apply the filter to each slice individually within a stack.

Figure 6:
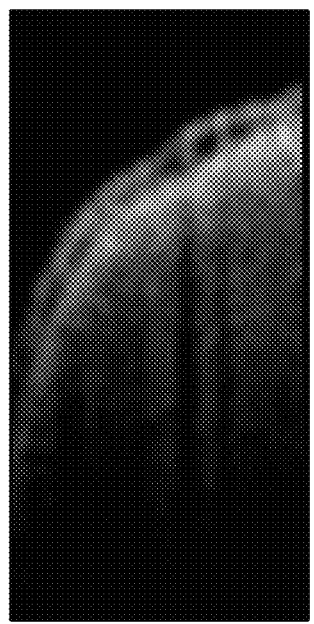
FIG. 6 is the slice of FIG. 4 subject to a blurring filter in accordance with an embodiment.

FIG. 6 shows a spatially smoothed, blurred slice 600. The blurred slice 600 may be processed from the slice 410. For example, the blurred slice 600 has a Gaussian blur applied to smooth out the intensity values. As can be seen in blurred slice 600, as compared to slice 410 of FIG. 5, the intensity is smoother and forms a blurred image of the slice.

After applying a smoothing operation, a processing unit, such as processing unit 1800 (see FIG. 18A), may perform a thresholding operation to create a corresponding segmented slice. The thresholding may be based off of the pixel intensities of the blurred slice, such as blurred slice 600. The thresholding operation may be a k-means method or a suitable thresholding operation to distinguish groups based off of pixel intensity.

Thresholding can involve dynamically selecting threshold values using Otsu's method to minimize intra-class intensity variance, or equivalently, maximize inter-class intensity variance.

Figure 7:
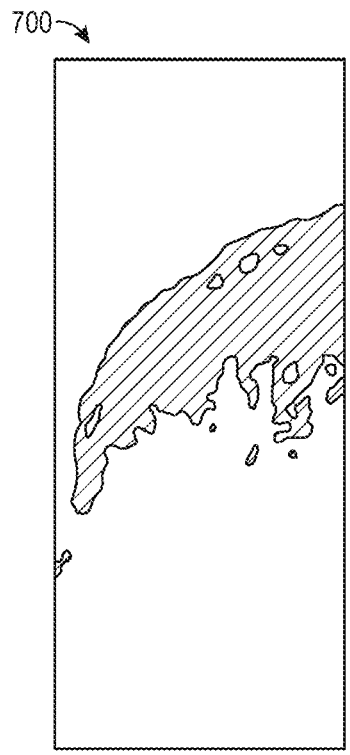
FIG. 7 is a segmented slice with identified blobs of the blurred slice of FIG. 6, according to an embodiment.

FIG. 7 shows corresponding segmented slice 700. Corresponding segmented slice 700 may come from a blurred slice, such as blurred slice 600, that has had a thresholding operation applied. For example, in a k-means method that thresholds into two groups based off of intensity, pixel intensities over a threshold value may be represented as white spots whereas pixel intensities below a threshold value become darkened. As a result, the image becomes a 2-dimensional image of regions with thresholded pixel intensities.

The threshold intensity may be based off of known pixel intensities for a measured brain surface. For example, a known measured brain surface intensity may be used as the thresholding value for an unknown brain to gauge the pixel intensity of the surface of the brain.

Comparing the corresponding segmented slice 700 with the blurred slice 600, there is a visual difference between the gradient intensity values of blurred slice 600 and the thresholded white on black of the corresponding segmented slice 700. For example, the lower intensity pixels close to the bottom of blurred slice 600 become empty/dark patches, providing a clear image of the regions with higher intensity signal that correspond to portions of the surface of the brain.

After a thresholding operation, the processing unit may use a connected-component analysis/operation to further define the surface of the brain. The connected-component operation groups connected regions based on the corresponding segmented slice. The connected component operation may look for continuity in the corresponding segmented slice and identify "blobs," or regions of threshold intensity values that form continuous structures. The processing unit may look at continuity to evaluate whether a region fulfills the qualifying pixel size of a blob. For example, the processing unit may look at each slice and set a threshold continuity of 10%, 20%, 30%, 40%, 50%, 60%, 70%, 80%, or 90% of the slice or more to qualify as a blob above the threshold value.

The continuity threshold may be based off of known brain heuristics and to assist in filtering out noise and artifacts that were captured by the OCT in processing each slice. For example, noisy signal and occlusions cast from the liquid or shadows would not have a continuity of greater than 50% of the slice, and thus, are subject to filtering out. In embodiments, the continuity threshold may be 60%, 70%, 80%, or 90%, or otherwise to properly filter out unwanted blobs.

Figure 8:
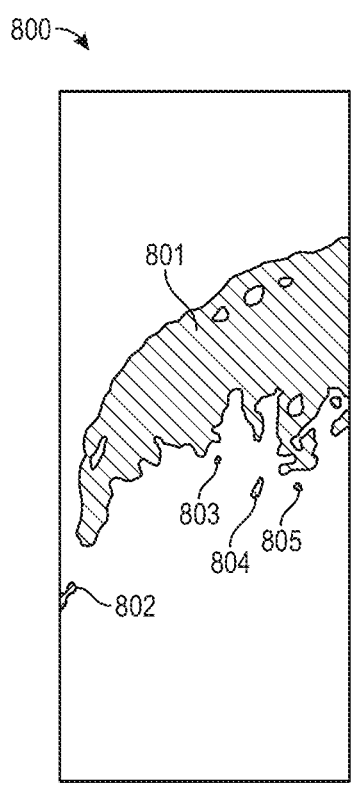
FIG. 8 is a segmented slice with filtered out blobs of the segmented slice of FIG. 7, according to an embodiment.

FIG. 8 is an example of a slice 800 with connected-component analysis performed on the corresponding segmented slice 700. As shown in the figure, slice 800 has blobs 801, 802, 803, 804, and 805. For example, blob 801 is a region of the brain corresponding to the surface. As blob 801 spans over 50% of the slide width, blob 801 would satisfy the threshold continuity length. However, blob 802, blob 803, blob 804, and blob 805 would be filtered out due to their blob sizes not satisfying the threshold continuity length of the slice 800.

After filtering the blobs based on a size, the processing unit may perform an edge detection on the blobs that have been filtered based on size.

Figure 9:
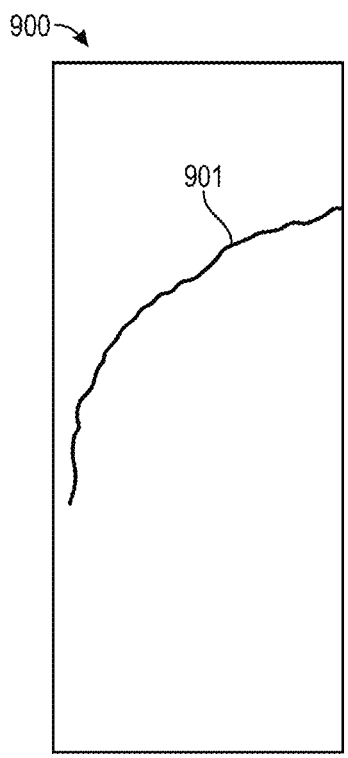
FIG. 9 is an edge detection slice based on the segmented slice of FIG. 8, according to an embodiment.

FIG. 9 shows an edge detection slice 900 that shows the result of an edge detection algorithm run on the blobs of slice 800. Blob 801 is above the threshold blob size, and thus, blob 801 is suitable for the edge detection algorithm. Slice 900 shows edge 901 that corresponds to the top edge of blob 801.

For speed, the edge detection algorithm may proceed only from the top of the slice to the bottom (i.e., in they direction only) instead of a more computationally expensive edge detection algorithms that finds edges from all angles.

The resultant edge 901 details the edge corresponding to the brain surface at a particular stack depth within the stack of slices. A processing unit may run a smoothing operation, thresholding operation, a connected component analysis, filtering, and edge detection on multiple slices in the stack in order to acquire the surface edge of the brain at varying depths corresponding to each slice.

From the resultant edges of the blobs of the stack of slices, a surface topology can be extracted using image derivatives and compiled into a 32-bit depth map. The slices can be ranked spatially according to known depths from the OCT measurement. The detected edges can be correlated to the real-world coordinates on the actual brain surface.

Figure 10:
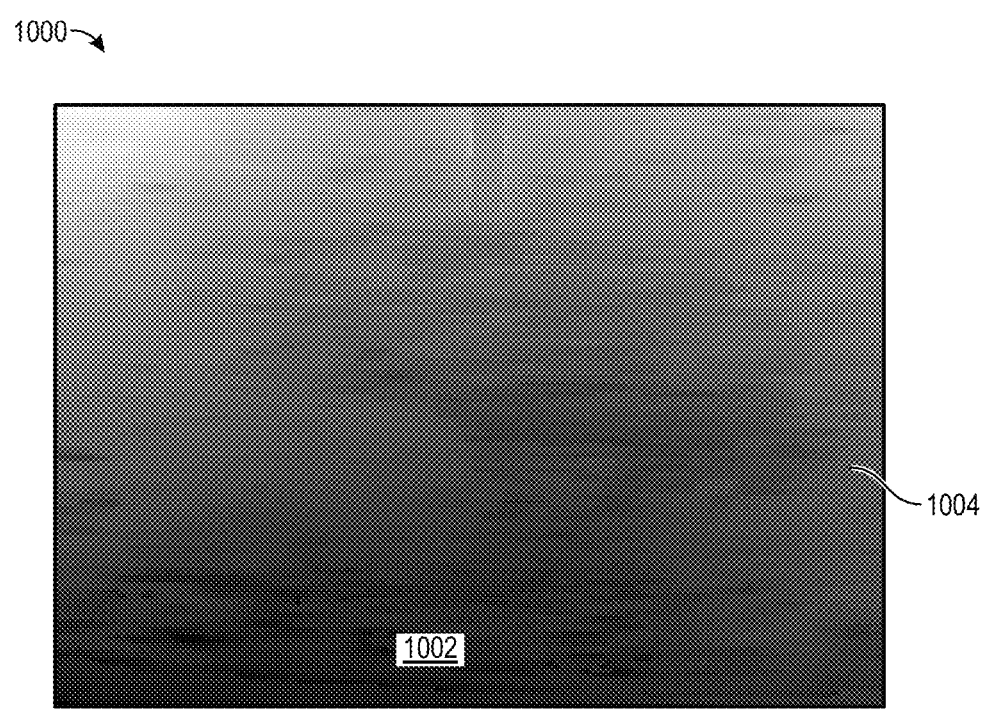
FIG. 10 is a depth map of a surface of a biological tissue constructed from the edge detection slice of FIG. 9 and others, according to an embodiment.

FIG. 10 shows a depth map 1000 of a surface topology based off of stack 400, according to embodiments. The depth map 1000 features the brain surface 1002 and a portion of the skull 1004. As shown in depth map 1000, the surface 1002 can be seen along the bottom of the depth map, which can help guide a robot inserter head, such as robot inserter head 102, in implanting electrodes to a surface of the brain. Furthermore, as an example, because the processing unit is aware of the portion of the skull 1004 to the right, the guidance of the robot inserter head can steer clear of potentially damaging the threads on bone. However, just the image derivative can produce noise and may not account for shadows of other electrodes or threads currently in the brain. These artifacts can present a false surface of the brain much higher than the actual surface of the brain.

In order to filter out any noise or shadows that provide an inaccurate depth map, a selective median filter can be used. The selective median filter may identify median points along the formed edges to create a surface topography. Moreover, because the selective median filter assesses the median value, the processing unit can confirm that a valid surface location is being selected, rather than a location in space that may occur with a selective mean filter.

Figure 11:
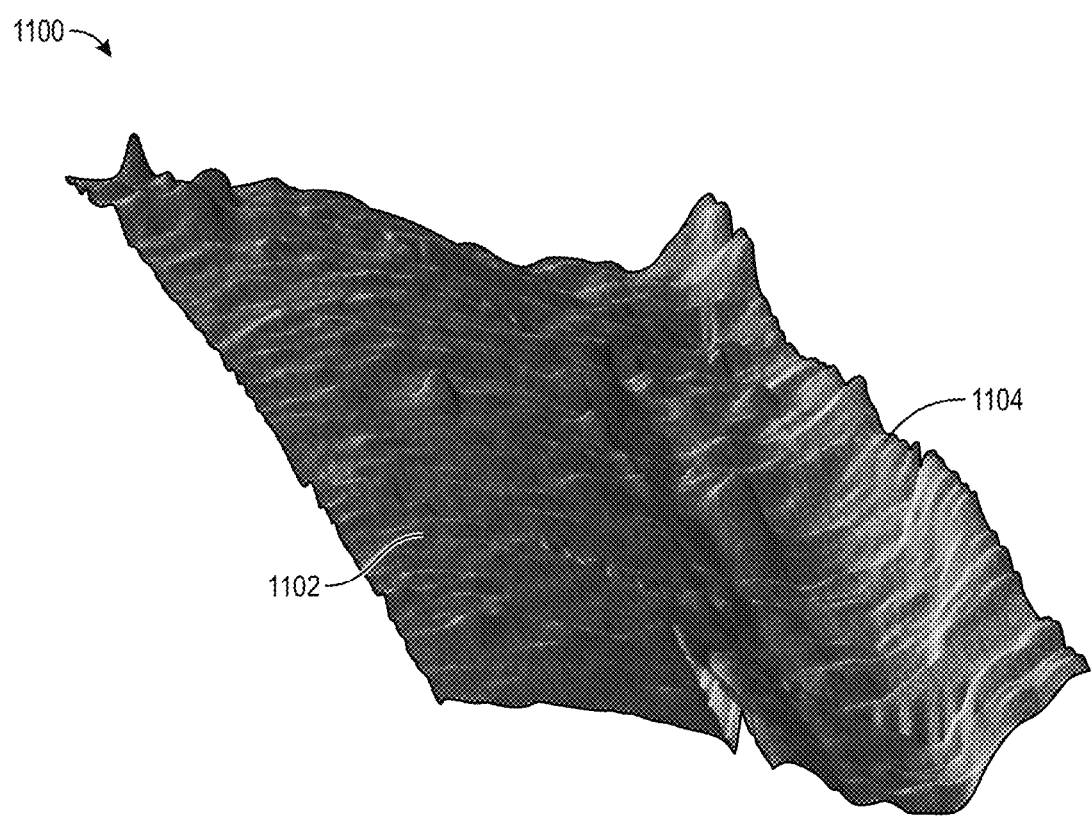
FIG. 11 is a 3-dimensional render of the depth map of FIG. 10, according to an embodiment.
Figure 12A:
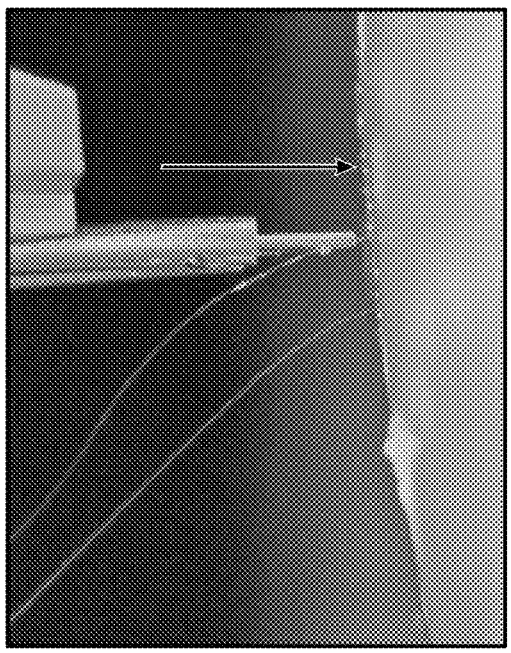
FIG. 12A illustrates pre-implantation of an electrode in a target tissue proxy substance, according to an embodiment.
Figure 12B:
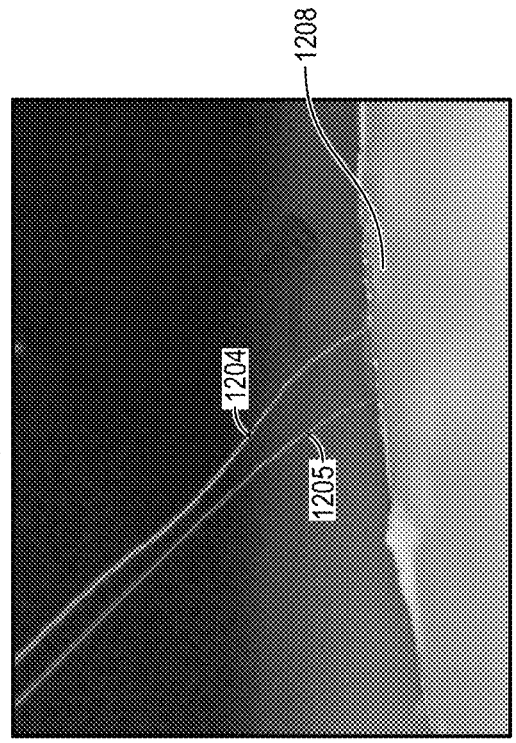
FIG. 12B illustrates lowering of a surgical robotic end effector of FIG. 12A.
Figure 12C:
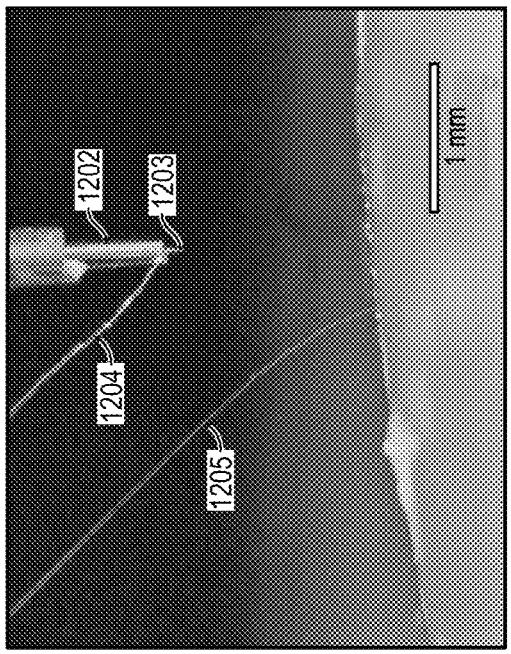
FIG. 12C illustrates insertion of an electrode into the target tissue proxy substance of FIG. 12A.
Figure 12D:
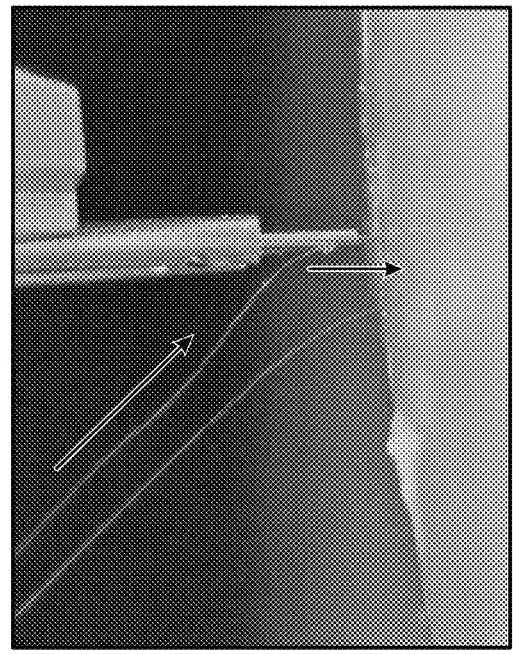
FIG. 12D illustrates the final thread electrode left in the target tissue proxy substance of FIG. 12A.

FIG. 11 shows a 3-D depth map 1100 of a brain surface after a selective median filter has been run on the depth map 1000 and several other depth maps. The 3-D depth map 1100 shows the brain surface 1102. The ridge on the right is the portion of the skull 1104. Based on the constructed depth map 1100, the processing unit can guide a robotic inserter head, such as inserter head 102, to implanting electrodes correctly along the surface of the brain.

Electrode Implantation

FIGS. 12A-12D illustrate implantation of electrodes in a target tissue proxy substance 1208, according to an embodiment. In particular, FIG. 12 shows a sequence of steps of the insertion process by an end effector of inserter head 1202 into an agarose brain tissue proxy. In this example, a needle 1203 first inserts a first thread 1205 on the left, which can hold a plurality of electrodes (e.g., 32 electrodes), and then inserts a second thread 1204 (shown in work), holding a second plurality of electrodes. The implantation can be guided by images acquired by OCT and a processing unit that obtains real-time data on the locations of the surface of implantation.

The inserter head 1202 support system holds an imaging stack used for guiding the needle into the thread loop, insertion targeting, live insertion viewing, and insertion verification. In addition, the inserter head contains light modules, each capable of independently illuminating with 405 nm, 525 nm and 650 nm or white light. A 405 nm illumination can excite fluorescence from polyimide and allow the optical stack and computer vision to reliably localize the (16×50) $\mu m^2$ thread loop and execute sub-micron visual serving to guide, illuminated by 650 nm the needle through it. Stereoscopic cameras, computer vision methods such as monocular extended depth of field calculations, and illumination with 525 nm light can allow for precise estimation of the location of the cortical surface while avoiding vasculature and other threads that may have been previously implanted.

The robot registers insertion sites to a common coordinate frame with landmarks on the skull, which, when combined with depth tracking, enables precise targeting of anatomically defined brain structures. Integrated custom computer instructions may allow pre-selection of all insertion sites, enabling planning of insertion paths optimized to minimize tangling and strain on the threads. The planning feature highlights the ability to avoid vasculature during insertions, one of the key advantages of inserting electrodes individually. This may provide a technical advantage, in order to avoid damage to the blood-brain barrier and thereby reduce inflammatory response. In an embodiment, the robot can feature an auto-insertion mode. While the entire insertion procedure can be automated, a surgeon can retain control, and can make manual micro-adjustments to the thread position before each insertion into the target tissue, such as a cortex. The neurosurgical robot is compatible with sterile shrouding, and has features to facilitate successful and rapid insertions such as automatic sterile ultrasonic cleaning of the needle.

Figure 13:
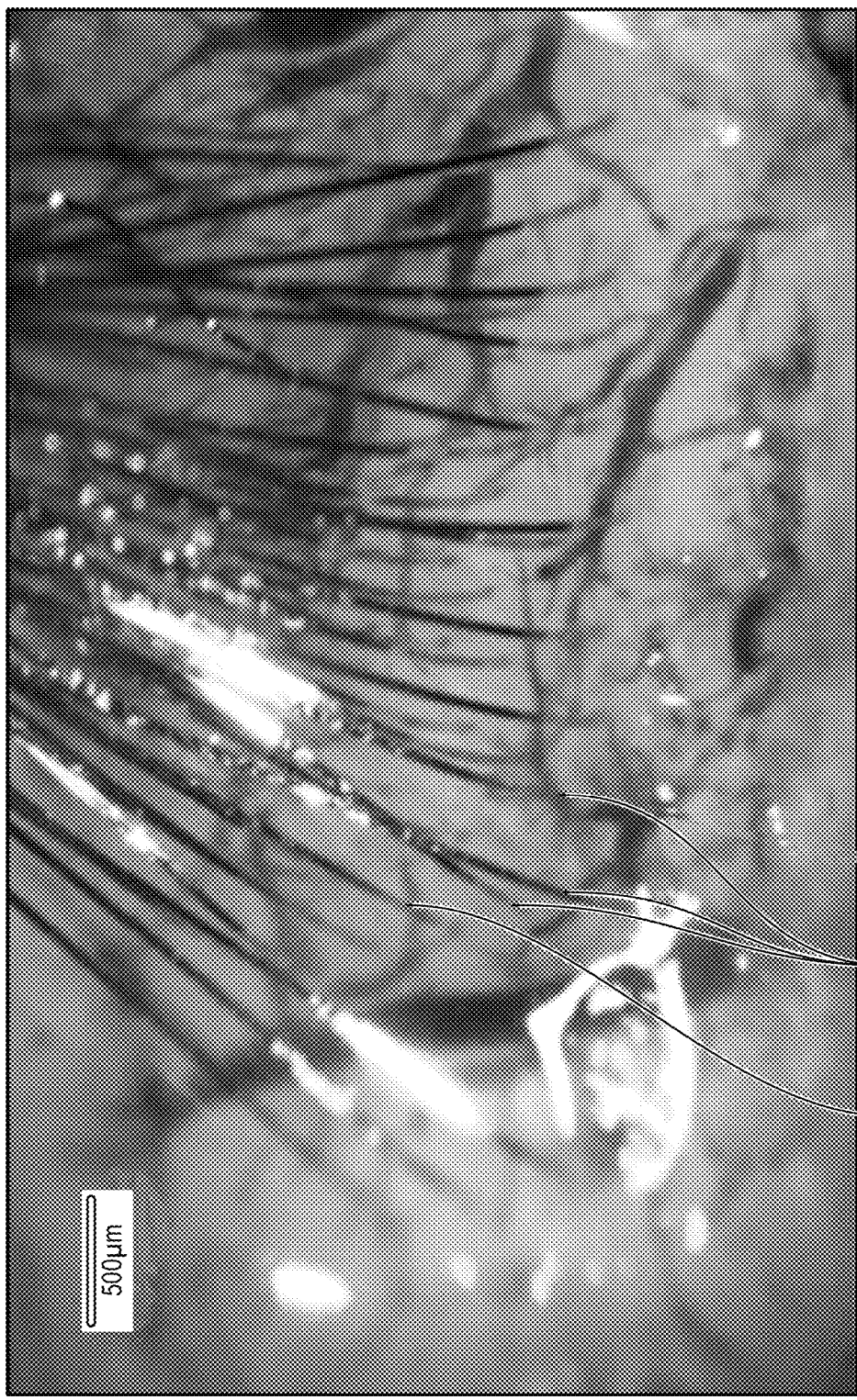
FIG. 13 illustrates an example of many electrodes implanted in brain tissue, according to an embodiment.

FIG. 13 illustrates an example of electrodes implanted in brain tissue, according to an embodiment. In a typical example, the disclosed system and methods may implant 96 polymer threads, such as threads 1308, into target tissue, each thread with 32 electrodes, for a total of 3,072 electrodes in the array. The electrodes are designed to be compact, thin, and flexible, with from 5 to 50 μm thread width and nominal thread thickness of 4 to 6 μm. In a typical example, the thread length can be approximately 20 mm. The small size and increased flexibility of these probes offers greater biocompatibility, enabling the probes to remain implanted for long periods of time without triggering immune responses. The small thread cross-sectional area can also minimize tissue displacement in the target.

Given the number of threads being inserted in a typical implantation operation, several of the initially inserted threads may be prone to casting shadows that impact computer vision for later inserted threads. For example, as can be seen in FIG. 13, the numerous threads 1308 are in close proximity with each other. During the course of implantation, previous threads must be accounted for by the processing unit in guiding the inserter head. While the example of FIGS. 5-9 depict a clean image of the brain surface, examples of the complexities of the environment of the brain can be seen below in FIGS. 14-16.

Figure 14:
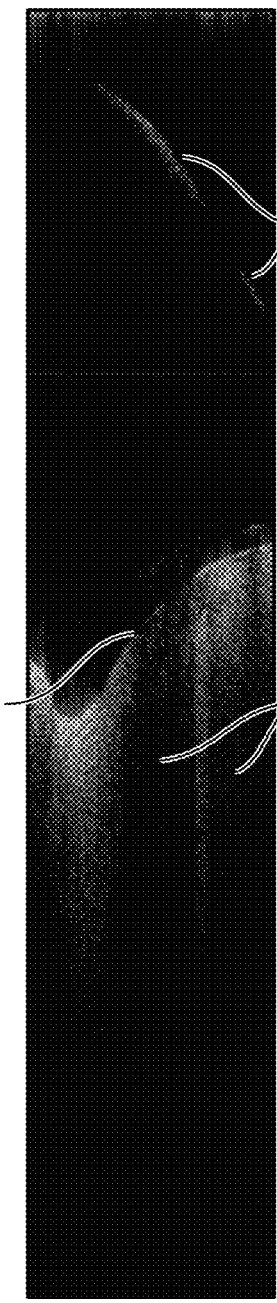
FIG. 14 illustrates an OCT a slice showing intensity values with a single thread, according to embodiments.

FIG. 14 shows a slice 1400 with intensity points measured by an OCT sensor, such as OCT sensor 110 (see FIG. 1B), with a thread casting a shadow across the brain surface. The slice 1400 shows regions 1401, 1402, and 1403. Region 1401 is the surface of the brain. The surface spanning across the slice would thus be the target of implantation. However, region 1402 represents a thread that casts a shadow. As can be seen by the drop in intensity at the region 1403, the thread in region 1402 impacts what is measured by the OCT sensor below. Due to the shadows cast, the resultant blob may be an inaccurate portrayal of the surface of the brain at that particular depth.

Figure 15:
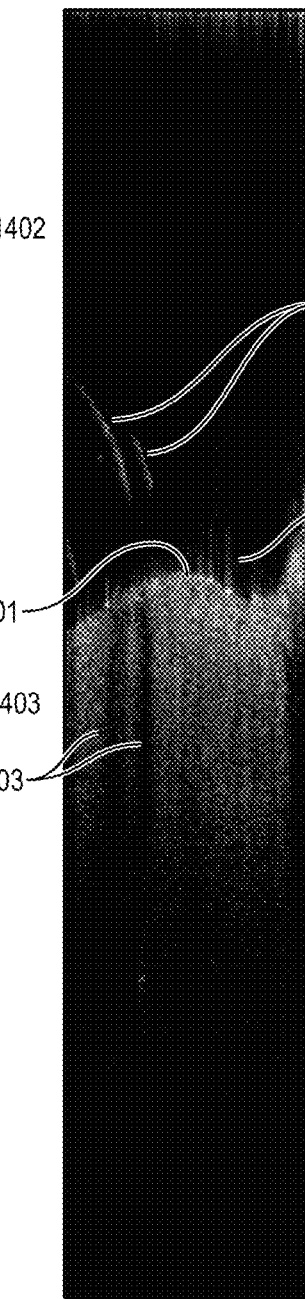
FIG. 15 illustrates an OCT a slice showing intensity values with multiple threads, according to embodiments.

FIG. 15 shows a slice 1500 with intensity points measured by an OCT sensor, such as OCT sensor 110 in FIG. 1B, with multiple threads casting shadows across the brain surface. The slice 1500 shows regions 1501, 1502, 1503, and 1504. Region 1501 is the surface of the brain. The region 1502 indicates multiple threads protruding from the surface of the brain. As can be seen by the drop in pixel intensity at the region 1503, the threads literally cast a shadow over the data below it acquired from the OCT sensor.

The artifacts observed at the region 1504 are caused by the refraction of light off of the fluid of the brain. The light sources used for OCT may refract off of the fluid on the brain when at certain angles, causing artifacts that are picked up as intensity values above the surface layer of the brain.

Figure 16:
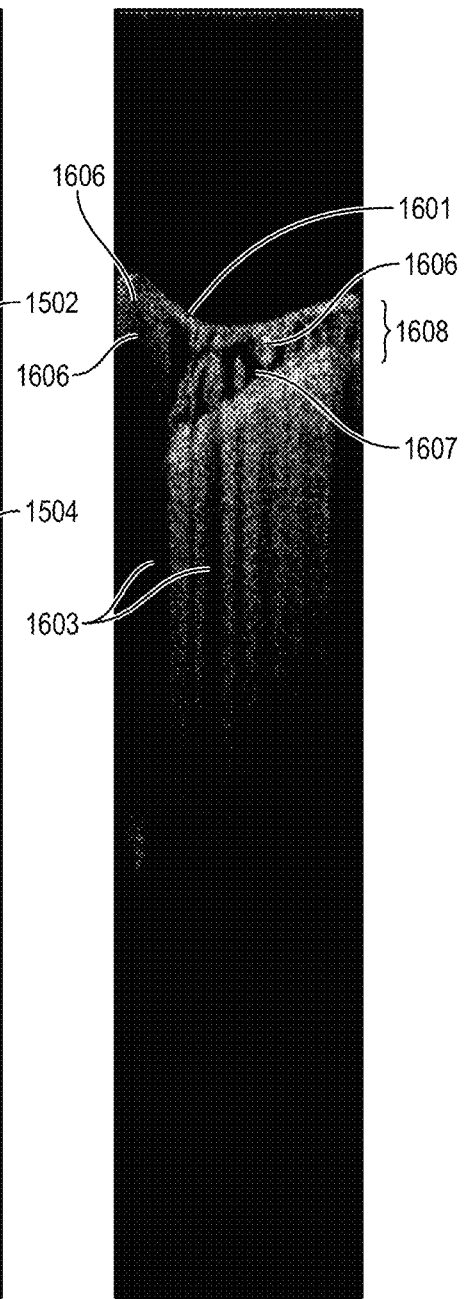
FIG. 16 illustrates an OCT a slice showing vasculature, vessels, and other artifacts in imaging, according to embodiments.

FIG. 16 shows a slice 1600 with intensity points measured by an OCT sensor, such as OCT sensor 110 in FIG. 1B, with vessels being imaged by the OCT sensor. The slice 1600 shows regions 1601, 1603, 1606, 1607, and 1608. Region 1601 is the surface of the brain. The shadows at region 1603 are occlusions cast from fluid and vessels along the surface of the brain. The high intensity regions 1606 represent blood vessels along the brain. The dark void region 1607 represents CSF flowing along the brain, which the OCT sensor have trouble picking up. The region 1608 collectively is the arachnoid space of the brain. The figure highlights the varying complexities that make using OCT data alone, without processing, a less precise metric for surgical operations in guiding a surgical robot.

Accordingly, use of the aforementioned filtering and processing methods improves the precision and accuracy of a surgical robot in implanting electrodes to neurons. Moreover, the above mentioned filtering and processing methods can be quick and efficient enough that a processed image will not have changed by the time the depth map has been generated. The filtering methods may not require lengthy processes to divide the data points, and the depth map generation does not require lengthy computation times.

The use of a selective median filter on the depth map allows for noise and artifacts, like those shown above, that may make it into the edge detection algorithm to be accounted for. In particular, when multiple electrodes are being implanted, it is important to avoid the previously implanted electrodes, and also important that previously implanted electrodes do not present a false surface mapping of the surface of the brain. Such a guiding error could result in implantation failure as well as breaking of the threads during operation.

Methods of Guiding Robotic Surgery

Figure 17:
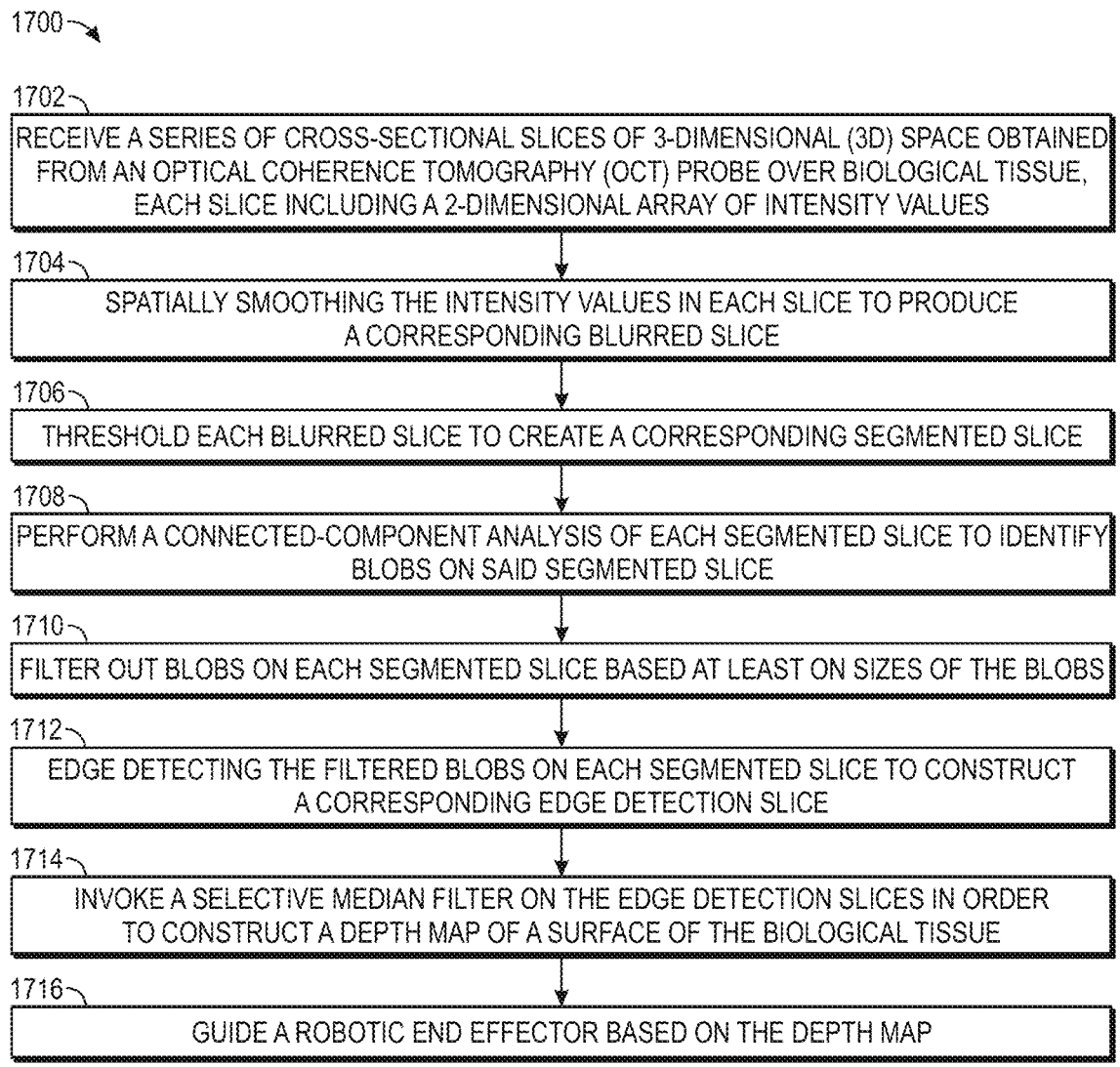
FIG. 17 is a method of guiding robotic surgery using optical coherence tomography, according to embodiments.

FIG. 17 is a flow chart illustrating an exemplary process 1700 for guiding robotic surgery, according to embodiments. In embodiments, the method can be used to guide a surgical robot to implant an electrode device within biological tissue. The step number of "first," "second," etc. is illustrative and not limiting to order or the exclusion of intermediate steps.

In a first step 1702, a series of cross-sectional slices of 3D space obtained from an OCT probe or sensor, such as the stack 400 of FIG. 4, is received, with each individual slice having a 2D array of light intensity values. The OCT probe or sensor can be the OCT sensor 110 in FIG. 1B. An exemplary slice can be seen as the slice 410 in FIG. 5.

In a second step 1704, the intensity values of each slice is spatially smoothed to produce a corresponding blurred slice. For example, the corresponding blurred slice 600 in FIG. 6 can be the slice 410 after it has been spatially smoothed.

In embodiments, the smoothing may be by a Gaussian blur. In embodiments, different smoothing functions, such as median blur, bilateral filter, or otherwise, can be applied to spatially smooth the slice.

In a third step 1706, each blurred slice is thresholded to create a corresponding segmented slice. Segmented slice 700 in FIG. 7 is an exemplary segmented slice, with a thresholding operation applied to identify pixel intensities received by the OCT sensor that are over a known value. The known pixel intensity may be based off of empirical data, known heuristics regarding the intensity of measured brain tissue, or otherwise.

In a fourth step 1708, a connected-component analysis is performed on each segmented slice to identify blobs, like the slice 800 in FIG. 8. The connected-component analysis examines connected components from the corresponding segmented slice, examining pixel relations after they have been thresholded. In embodiments, performing the connected-component analysis can provide for spatial information regarding the surface of the brain at a particular depth.

In a fifth step 1710, blobs are filtered out on each segmented slice based on at least the size of the blobs. In embodiments, the blob size can be known based off of empirical data from known measured blobs. In embodiments, the filtering can be based on the continuity of a blob in proportion to the width of a particular slice. For example, blobs may be filtered off of 50%, 60%, 70%, 80%, or 90% continuity across a slice, or in other proportions as applications allow.

In embodiments, the filtering can be based on the continuity of a blob in proportion to the width of a particular slice. For example, blobs may be filtered off of 50%, 60%, 70%, 80%, or 90% continuity across a slice. Optionally, the filtering process may remove a blob that does not project at least 50%, 75%, or 90% across a segmented slice.

In a sixth step 1712, edge detection is performed on the filtered blobs on each segmented slice, for example, like the edge detection slice 900 of FIG. 9. The edge detection identifies an edge of each blob that was not filtered out in previous step 1710.

In a seventh step 1714, a selective median filter is invoked on the edge detection slices to construct a depth map of a surface of the biological tissue, like the depth map 1000 of FIG. 10. The edge detection of each slice in a stack, such as stack 400, may be put together to form a depth map, such as depth map 1000, showing the depth map of a region of the brain. In embodiments, a system, such as system 100 (see FIG. 1A), may be able to relate the coordinates of a stack to its tissue location. The selective median filter may provide for a median value of the surface, which may aid in filtering out noise and artifacts from the sensor, occlusion from fluid, or other threads already implanted in the brain.

In an eighth step 1716, a robotic end effector is guided based on the depth map. In embodiments, the robotic end effector is controlled by a surgical robot, such as that of system 100 (see FIG. 1A). The depth map may guide the surgical robot in accurately and precisely moving to a desired region of the brain. In embodiments, this may be guiding an inserter head, such as inserter head 102.

Figure 18A:
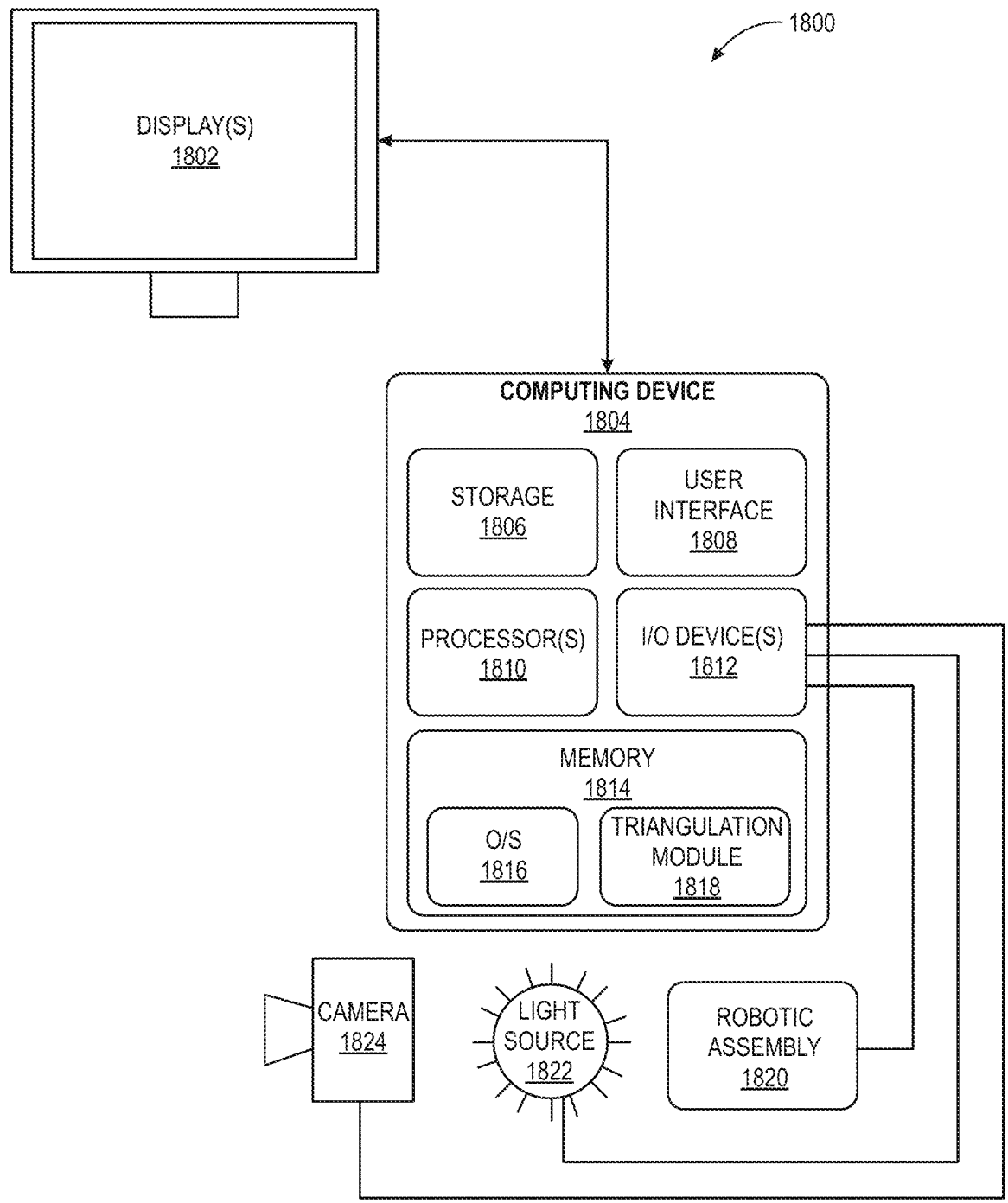
FIG. 18A illustrates an example computing system for robotic surgery guided by computer vision using optical coherence tomography, according to embodiments.

FIG. 18A illustrates components of an example computing system 1800, according at least one example. Computing system 1800 can include one or more display devices such as display devices 1802. The display devices 1802 may be any suitable devices capable of visually presenting information. Examples of such devices may include cathode ray tube (CRT) displays, light-emitting diode (LED) displays, electroluminescent displays (ELD), electronic paper, plasma display panels (PDP), liquid crystal displays (LCD), organic light-emitting diode (OLED) displays, surface-conduction electron-emitter displays (SED), field emission displays (FED), projectors (LCD, CRT, digital light processing (DLP), liquid crystal on silicon (LCoS), LED, hybrid LED, laser diode), and any other suitable device capable of displaying information.

Computing system 1800 may include computing device 1804, which may be connected to the robotic assemblies 1820, light sources 1822, and cameras 1824, as well as to any other devices, such as actuators, etc. The computing device 1804 may be in communication with these devices and/or other components of the robotic surgery system via one or more network(s), wired connections, and the like. The network may include any one or a combination of many different types of networks, such as cable networks, the Internet, wireless networks, cellular networks, radio networks, and other private and/or public networks.

Turning now to the details of the computing device 1804, the computing device 1804 may include at least one memory 1814 and one or more processing units (or processor(s)) 1810. The processor(s) 1810 may be implemented as appropriate in hardware, computer-executable instructions, software, firmware, or combinations thereof. For example, the processor(s) 1810 may include one or more general purpose computers, dedicated microprocessors, or other processing devices capable of communicating electronic information. Examples of the processor(s) 1810 include one or more application-specific integrated circuits (ASICs), field programmable gate arrays (FPGAs), digital signal processors (DSPs) and any other suitable specific or general purpose processors.

Computer-executable instruction, software, or firmware implementations of the processor(s) 1810 may include computer-executable or machine-executable instructions written in any suitable programming language to perform the various functions described. The memory 1814 may include more than one memory and may be distributed throughout the computing device 1804. The memory 1814 may store program instructions (e.g., a triangulation module 1818) that are loadable and executable on the processor(s) 1810, as well as data generated during the execution of these programs. Depending on the configuration and type of memory including the triangulation module 1818, the memory 1814 may be volatile (such as random access memory (RAM)) and/or non-volatile (such as read-only memory (ROM), flash memory, or other memory). In an embodiment, the triangulation module 1818 may receive and/or adjust the linear combination coefficients for Laplacian estimation based on the potentials measured by the CRE. In an embodiment, triangulation module 1818 may implement the linear combination based on these coefficients. The computing device 1804 may also include additional removable and/or non-removable storage 1806 including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 1814 may include multiple different types of memory, such as static random access memory (SRAM), dynamic random access memory (DRAM), or ROM. The memory 1814 may also include an operating system 1816.

The memory 1814 and the additional storage 1806, both removable and non-removable, are examples of computer-readable storage media. For example, computer-readable storage media may include volatile or non-volatile, removable, or non-removable media implemented in any suitable method or technology for storage of information such as computer-readable instructions, data structures, program modules, or other data. As used herein, modules may refer to programming modules executed by computing systems (e.g., processors) that are part of the triangulation module 1818. The modules of the triangulation module 1818 may include one or more components, modules, and the like. For example, triangulation module 1818 may include modules or components that triangulate the location of objects such as electrodes, insertion needles, and/or target tissue based on computer vision. The computing device 1804 may also include input/output ("I/O") device(s) and/or ports 1812, such as for enabling connection with a keyboard, a mouse, a pen, a voice input device, a touch input device, a display, speakers, a printer, or other I/O device. The I/O device(s) 1812 may enable communication with the other systems of the robotic surgery system.

The computing device 1804 may include a user interface 1808. The user interface 1808 may be utilized by an operator or other authorized user such as the user to access portions of the computing device 1804 (e.g., the triangulation module 1818). In some examples, the user interface 1808 may include a graphical user interface, web-based applications, programmatic interfaces such as application programming interfaces (APIs), or other user interface configurations.

Figure 18B:
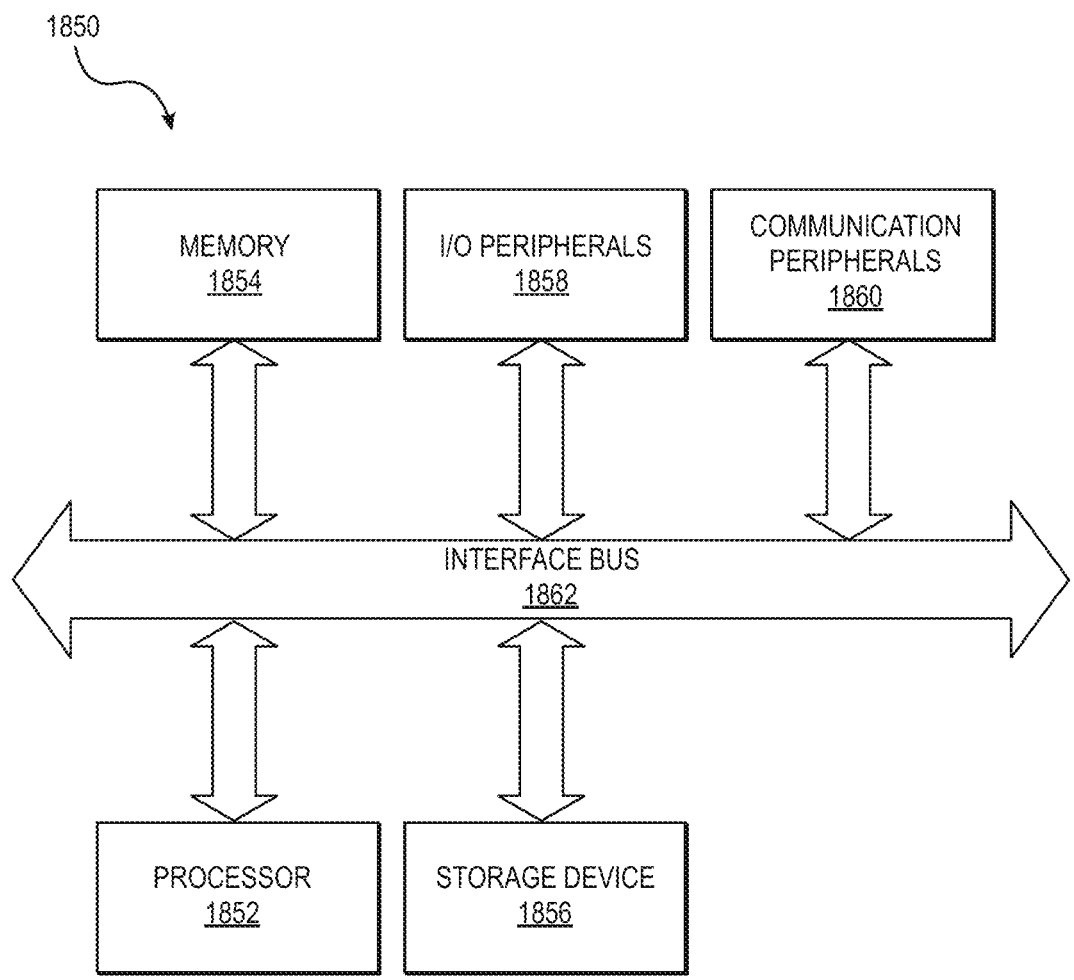
FIG. 18B illustrates example components computing system for robotic surgery guided by computer vision using optical coherence tomography, according to embodiments.

FIG. 18B illustrates examples of components of a computer system 1850, according to at least one example. The computer system 1850 may be a single computer such as a user computing device and/or can represent a distributed computing system such as one or more server computing devices.

The computer system 1850 may include at least a processor 1852, a memory 1854, a storage device 1856, input/output peripherals (I/O) 1858, communication peripherals 1185, and an interface bus 1862. The interface bus 1862 is configured to communicate, transmit, and transfer data, controls, and commands among the various components of the computer system 1850. The memory 1854 and the storage device 1856 include computer-readable storage media, such as Radom Access Memory (RAM), Read ROM, electrically erasable programmable read-only memory (EEPROM), hard drives, CD-ROMs, optical storage devices, magnetic storage devices, electronic non-volatile computer storage, for example Flash® memory, and other tangible storage media. Any of such computer-readable storage media can be configured to store instructions or program codes embodying aspects of the disclosure. The memory 1854 and the storage device 1856 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the computer system 1850.

Further, the memory 1854 includes an operating system, programs, and applications. The processor 1852 is configured to execute the stored instructions and includes, for example, a logical processing unit, a microprocessor, a digital signal processor, and other processors. The memory 1854 and/or the processor 1852 can be virtualized and can be hosted within another computing system of, for example, a cloud network or a data center. The I/O peripherals 1858 include user interfaces, such as a keyboard, screen (e.g., a touch screen), microphone, speaker, other input/output devices, and computing components, such as graphical processing units, serial ports, parallel ports, universal serial buses, and other input/output peripherals. The I/O peripherals 1858 are connected to the processor 1852 through any of the ports coupled to the interface bus 1862. The communication peripherals 1185 are configured to facilitate communication between the computer system 1850 and other computing devices over a communications network and include, for example, a network interface controller, modem, wireless and wired interface cards, antenna, and other communication peripherals.

The terms "computing system" and "processing unit" as used herein are intended for all purposes to be interpreted broadly and is defined for all uses, all devices, and/or all systems and/or systems in this disclosure as a device comprising at least a central processing unit, a communications device for interfacing with a data network, transitory computer-readable memory, and/or a non-transitory computer-readable memory and/or media. The central processing unit carries out the instructions of one or more computer programs stored in the non-transitory computer-readable memory and/or media by performing arithmetical, logical, and input/output operations to accomplish in whole or in part one or more steps of any method described herein. A computing system is usable by one or more users, other computing systems directly and/or indirectly, actively and/or passively for one or more suitable functions herein. The computing system may be embodied as computer, a laptop, a tablet computer, a smartphone, and/or any other suitable device and may also be a networked computing system, a server, or the like. Where beneficial, a computing system can include one or more human input devices such as a computer mouse and/or keyboard and one or more human interaction device such as one or more monitors. A computing system may refer to any input, output, and/or calculating device associated with providing an experience to one or more users. Although one computing system may be shown and/or described, multiple computing systems may be used. Conversely, where multiple computing systems are shown and/or described, a single computing device may be used.

A "pia-arachnoid complex" typically includes arachnoid and pia mater. Arachnoid includes arachnoid mater and subarachnoid space containing cerebrospinal fluid (CSF). The pia mater is an approximately single-cell layer conformal to the cortex.

It is known that there are shadows from vasculature, so that information is used to match potential vascular boundaries in one image to potential vascular boundaries in other images. It is also known that three other surfaces, including the CSF, pia, and cortex surfaces, should be present. A real-time algorithm can use this information to pre-determine areas that should have surfaces and thus narrow down their search.

It should be appreciated that a brain implant or other system and a respective control system for the brain implant can have one or more microprocessors/processing devices that can further be a component of the overall apparatuses. The control systems are generally proximate to their respective devices, in electronic communication (wired or wireless) and can also include a display interface and/or operational controls configured to be handled by a user to monitor the respective systems, to change configurations of the respective systems, and to operate, directly guide, or set programmed instructions for the respective systems, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C #, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

In some embodiments, the systems and methods of the present disclosure can be used in connection with neurosurgical techniques. However, one skilled in the art would recognize that neurosurgical techniques are a non-limiting application, and the systems and methods of the present disclosure can be used in connection with any biological tissue. Biological tissue can include, but is not limited to, the brain, muscle, liver, pancreas, spleen, kidney, bladder, intestine, heart, stomach, skin, colon, and the like.

The systems and methods of the present disclosure can be used on any suitable multicellular organism including, but not limited to, invertebrates, vertebrates, fish, bird, mammals, rodents (e.g., mice, rats), ungulates, cows, sheep, pigs, horses, non-human primates, and humans. Moreover, biological tissue can be ex vivo (e.g., tissue explant), or in vivo (e.g., the method is a surgical procedure performed on a patient).

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A method of guiding robotic surgery, the method comprising:
   receiving a series of cross-sectional slices of 3-dimensional (3D) space obtained from an optical coherence tomography (OCT) probe over biological tissue, each slice of the series including a 2-dimensional array of intensity values;
   spatially smoothing the intensity values in each slice to produce a corresponding blurred slice;
   thresholding each blurred slice to create a corresponding segmented slice;
   performing a connected-component analysis of each segmented slice to identify blobs on said segmented slice;
   determining a span for each blob, the span measuring a width across a respective segmented slice that the blob projects;
   filtering out blobs on each segmented slice based on the spans of the blobs;
   edge detecting the filtered blobs on each segmented slice to construct a corresponding edge detection slice;
   invoking a selective median filter on the edge detection slices in order to construct a depth map of a surface of the biological tissue; and
   guiding a robotic end effector based on the depth map.

2. The method of claim 1 further comprising:
   removing from consideration a segmented slice whose largest blob does not project at least 50% across said segmented slice.

3. The method of claim 2 wherein the largest blob does not project at least 75% across said segmented slice.

4. The method of claim 1 wherein the filtering out rejects a blob corresponding to an electrical wire protruding from the biological tissue.

5. The method of claim 1 wherein the biological tissue is brain cortex covered with pia-arachnoid complex.

6. The method of claim 1 wherein the spatially smoothing includes Gaussian blurring or median blurring.

7. The method of claim 1 wherein the thresholding involves dynamically selecting threshold values using Otsu's method to minimize intra-class intensity variance.

8. The method of claim 1 further comprising:
   selecting the series of slices from a larger set of OCT slices.

9. The method of claim 1 wherein the edge detecting results in more than one continuous edge in each edge detection slice.

10. The method of claim 1 wherein the selective median filter creates multiple depth maps of surfaces of the biological tissue, the method further comprising:
    selecting a top surface depth map for guiding the robotic end effector.

11. A machine-readable non-transitory medium embodying information for guiding robotic surgery, the information indicative of instructions for causing one or more machines to perform operations comprising:
    receiving a series of cross-sectional slices of 3-dimensional (3D) space obtained from an optical coherence tomography (OCT) probe over biological tissue, each slice of the series including a 2-dimensional array of intensity values;
    spatially smoothing the intensity values in each slice to produce a corresponding blurred slice;
    thresholding each blurred slice to create a corresponding segmented slice;
    performing a connected-component analysis of each segmented slice to identify blobs on said segmented slice;
    determining a span for each blob, the span measuring a width across a respective segmented slice that the blobs projects;
    filtering out blobs on each segmented slice based on the spans of the blobs;
    edge detecting the filtered blobs on each segmented slice to construct a corresponding edge detection slice;
    invoking a selective median filter on the edge detection slices in order to construct a depth map of a surface of the biological tissue; and
    guiding a robotic end effector based on the depth map.

12. The machine-readable medium of claim 11 further comprising:
removing from consideration a segmented slice whose largest blob does not project at least 50% across said segmented slice.

13. The machine-readable medium of claim 12 wherein the largest blob does not project at least 75% across said segmented slice.

14. The machine-readable medium of claim 11 wherein the spatially smoothing includes Gaussian blurring or median blurring.

15. The machine-readable medium of claim 11 wherein the thresholding involves dynamically selecting threshold values using Otsu's method to minimize intra-class intensity variance.

16. A computer system executing program code for guiding robotic surgery, the computer system comprising:
a memory; and
at least one processor operatively coupled with the memory and executing program code from the memory comprising instructions for:
receiving a series of cross-sectional slices of 3-dimensional (3D) space obtained from an optical coherence tomography (OCT) probe over biological tissue, each slice of the series including a 2-dimensional array of intensity values;
spatially smoothing the intensity values in each slice to produce a corresponding blurred slice;
thresholding each blurred slice to create a corresponding segmented slice;
performing a connected-component analysis of each segmented slice to identify blobs on said segmented slice;
determining a span for each blob, the span measuring a width across a respective segmented slice that the blob projects;
filtering out blobs on each segmented slice based on the spans of the blobs;
edge detecting the filtered blobs on each segmented slice to construct a corresponding edge detection slice;
invoking a selective median filter on the edge detection slices in order to construct a depth map of a surface of the biological tissue; and
guiding a robotic end effector based on the depth map.

17. The computer system of claim 16 further comprising:
removing from consideration a segmented slice whose largest blob does not project at least 50% across said segmented slice.

18. The computer system of claim 17 wherein the largest blob does not project at least 75% across said segmented slice.

19. The computer system of claim 16 wherein the spatially smoothing includes Gaussian blurring or median blurring.

20. The computer system of claim 16 wherein the thresholding involves dynamically selecting threshold values using Otsu's method to minimize intra-class intensity variance.

* * * * *